(12) United States Patent
Boaz et al.

(10) Patent No.: US 7,566,795 B2
(45) Date of Patent: Jul. 28, 2009

(54) PREPARATION OF RETINYL ESTERS

(75) Inventors: Neil Warren Boaz, Kingsport, TN (US); Stephanie Kay Clendennen, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 11/544,152

(22) Filed: Oct. 6, 2006

(65) Prior Publication Data

US 2008/0085534 A1    Apr. 10, 2008

(51) Int. Cl.
C07C 59/00 (2006.01)
C12P 7/64 (2006.01)
C12P 23/00 (2006.01)

(52) U.S. Cl. .......................... 554/214; 435/67; 435/134

(58) Field of Classification Search ........................ None
See application file for complete search history.

(56) References Cited

U.S. PATENT DOCUMENTS

| | | | | |
|---|---|---|---|---|
| 5,232,843 A | * | 8/1993 | Bosley et al. | 435/135 |
| 5,902,738 A | * | 5/1999 | Orsat et al. | 435/155 |
| 2003/0175918 A1 | * | 9/2003 | Basheer | 435/176 |

FOREIGN PATENT DOCUMENTS

| | | | |
|---|---|---|---|
| EP | 1 775 344 A2 | | 4/2007 |
| JP | 62-248495 | * | 10/1987 |
| WO | WO 03/104183 A1 | | 5/2003 |

OTHER PUBLICATIONS

Maugard et al., "Enzymatic synthesis of derivatives of vitamin A in organic media," Journal of Molecular Catalysis B: Enzymatic 8, Jun. 1999, pp. 275-280.*
Maugard et al., "Synthesis of Water-Soluble Retinol Derivatives byEnzymatic Method," Biotechnol. Prog., May 2002, pp. 424-428, vol. 18.*
O'Connor et al., "*Candida cylindracea* Lipase-Catalysed Synthesis of Retinyl and Oleyl Palmitates; Carbon Chain Length Dependence of Esterase Activity," Aust. J. Chem., 1992, pp. 641-649, vol. 45.*
Marpat, 140:19612 of EP 1369411, Dec. 2003.*
Yin et al.,Chinese Journal of Chemical Engineering (2006), 14(1), pp. 81-86.*
Tan et al, Chem. Abstr. of CN 1621528, 2005.*
Maugard et al., "Study of Vitamin Ester Synthesis by Lipase-Catalyzed Transesterification in Organic Media," Biotechnol. Prog., Jun. 2000, pp. 358-362, vol. 16.
Maugard et al., "Synthesis of Water-Soluble Retinol Derivatives by Enzymatic Method," Biotechnol. Prog., May 2002, pp. 424-428, vol. 18.
Notification of Transmittal of the International Search Report and the Written Opinion of the International Searching Authority, or the Declaration date of mailing Apr. 23, 2008 for corresponding International Application No. PCT/US2007/020185.
Liu, T. et al.; "Lipase catalyzed synthesis of vitamin A esters"; vol. 25, No. 2; Feb. 2005; pp. 37-40.

* cited by examiner

*Primary Examiner*—Deborah D Carr
(74) *Attorney, Agent, or Firm*—Brett L Nelson; Bernard J. Graves, Jr.

(57) ABSTRACT

Long-chain esters of retinol are prepared via a chemoenzymatic process from short-chain retinyl esters and an appropriate long-chain acid or ester in the presence of an enzyme. Use of various additives enhance the yield of the desired ester and facilitated its purification.

37 Claims, No Drawings

PREPARATION OF RETINYL ESTERS

FIELD OF THE INVENTION

The present invention relates to the preparation of long-chain esters of retinol via chemoenzymatic processing from short-chain retinyl esters and an appropriate long-chain acid or ester in the presence of an enzyme.

BACKGROUND

Retinol (Vitamin A) and retinyl esters have long been added to cosmetic compositions to provide topical benefits. Retinol itself is unstable and is toxic with excessive use. Long-chain retinyl esters, however, are preferred because they are more stable.

The classical chemical preparation of long-chain retinyl esters involves either the reaction of retinol with a long chain acid, acid chloride or an ester or by the transesterification of a short-chain retinyl ester with a long-chain fatty acid ester. These processes use either harsh reagents or high temperatures, which can cause difficulties due to the instability of retinol or the retinyl esters to these types of reaction conditions.

There have been several reports of chemoenzymatic syntheses of long-chain retinyl esters. Many of these syntheses utilize expensive and unstable retinol as the starting material (O'Connor et. al. *Aust. J. Chem.* 1992, 45, 641; Maugard, et. al. *J. Mol. Catal. B: Enzymatic* 2000, 8, 275; Maugard et. al., *Biotechnol. Prog.* 2000, 16, 358; Maugard et. al. *Biotechnol. Prog.* 2002, 18, 424.). Retinyl esters such as retinyl acetate are much more stable and significantly less expensive than retinol, and several reports have utilized this material as the starting material for a biocatalytic preparation of long-chain retinyl esters. An unexamined Japanese Patent Application (JP 62-248495, 1987) utilized vitamin A acetate and a fatty acid in an organic solvent with a lipase modified with O-methoxypolyethylene glycol to prepare long-chain retinyl esters. Although reasonable yields of the desired products are obtained, this process requires a separate modification of the lipase for success. A process which did not require this modification would be more desirable. International Patent Application WO 2004/044212 A1 details a biocatalytic synthesis of long-chain retinyl esters from retinol or a retinyl ester and a fat or oil of animal or vegetable origins under solvent-free conditions. Unfortunately, this process utilizes elevated temperatures and results in only moderate conversions (17-44%) to the desired product, which could complicate isolation. A mild process for the preparation of long-chain retinyl esters from readily available precursors would therefore be of interest.

SUMMARY OF THE INVENTION

A first embodiment of the present invention concerns a process for preparing a retinyl ester. The method includes reacting a short-chain retinyl ester according to formula 2:

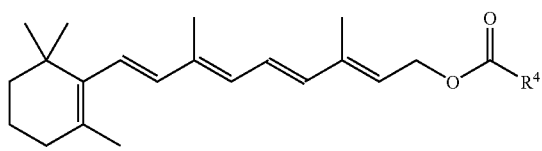

with a long-chain acid or long-chain ester in the presence of an organic solvent and an enzyme to form the retinyl ester. $R^4$ is selected from the group consisting of hydrogen, $C_1$-$C_4$ alkyl groups and $C_2$-$C_4$ alkenyl groups.

Another embodiment concerns process for the preparation of long-chain retinyl ester compounds represented by the general formula 1:

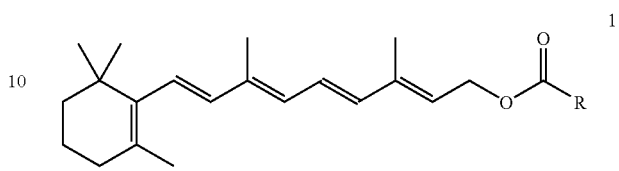

The method according to this embodiment includes reacting a short-chain retinyl ester with a long-chain acid or long-chain ester in the presence of an organic solvent and an enzyme and optionally in the presence of at least one molecular sieve and/or at least one ion exchange resin to form the retinyl ester. R is selected from at least one of the group consisting of $C_4$-$C_{24}$ alkyl, $C_4$-$C_{24}$ alkenyl, $C_5$-$C_{24}$ dienyl, $C_6$-$C_{24}$ trienyl, $C_8$-$C_{24}$ tetraenyl, $C_3$-$C_8$ cycloalkyl, $C_6$-$C_{20}$ carbocyclic aryl, $C_4$-$C_{20}$ heteroaryl, and mixtures thereof, wherein the heteroaryl includes at least one of sulfur, nitrogen and oxygen.

DETAILED DESCRIPTION OF THE INVENTION

The present invention concerns a process for the preparation of long-chain retinyl ester compounds represented by the general formula 1:

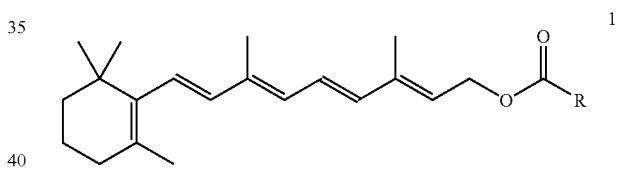

wherein
R is selected from substituted and unsubstituted, branched- and straight-chain, saturated, unsaturated, and polyunsaturated $C_4$-$C_{20}$ alkyl, substituted and unsubstituted $C_3$-$C_8$ cycloalkyl, substituted and unsubstituted $C_6$-$C_{20}$ carbocyclic aryl, substituted and unsubstituted $C_4$-$C_{20}$ heteroaryl, and mixtures thereof wherein the heteroatoms are selected from sulfur, nitrogen, and oxygen;

Preferred species are denoted by structure 1 wherein R is selected from substituted and unsubstituted, branched- and straight-chain saturated, $C_4$-$C_{24}$ alkyl, substituted and unsubstituted, branched- and straight-chain $C_4$-$C_{24}$ alkenyl, substituted and unsubstituted, branched- and straight-chain $C_4$-$C_{24}$ dienyl, substituted and unsubstituted, branched- and straight-chain $C_6$-$C_{24}$ trienyl, and substituted and unsubstituted, branched- and straight-chain $C_8$-$C_{24}$ tetraenyl or mixtures thereof.

The alkyl, alkenyl, dienyl, trienyl, and tetraenyl groups which may be represented by R may be straight- or branched-chain aliphatic hydrocarbon radicals containing up to about 24 carbon atoms and may be substituted, for example, with one to three groups selected from $C_1$-$C_6$-alkoxy, cyano, $C_2$-$C_6$-alkoxycarbonyl, $C_2$-$C_6$-alkanoyloxy, hydroxy, aryl, heteroaryl, thiol, thioether, disulfide, and halogen. The terms "$C_1$-$C_6$-alkoxy", "$C_2$-$C_6$-alkoxycarbonyl", and "$C_2$-$C_6$-alkanoyloxy" are used to denote radicals corresponding to the structures —OR$^2$, —CO$_2$R$^2$, and —OCOR$^2$, respectively, wherein R$^2$ is C$_1$-C$_6$-alkyl or substituted C$_1$-C$_6$-alkyl. The term "C$_3$-C$_8$-cycloalkyl" is used to denote a saturated, carbocyclic hydrocarbon radical having three to eight carbon atoms.

The aryl groups which R may represent may include phenyl, naphthyl, or anthracenyl and phenyl, naphthyl, or anthracenyl substituted with one to three substituents selected from C$_1$-C$_6$-alkyl, substituted C$_1$-C$_6$-alkyl, C$_6$-C$_{10}$ aryl, substituted C$_6$-C$_{10}$ aryl, C$_1$-C$_6$-alkoxy, halogen, carboxy, cyano, C$_1$-C$_6$-alkanoyloxy, C$_1$-C$_6$-alkylthio, C$_1$-C$_6$-alkylsulfonyl, trifluoromethyl, hydroxy, C$_2$-C$_6$-alkoxycarbonyl, C$_2$-C$_6$-alkanoylamino and —O—R$^3$, S—R$^3$, —SO$_2$—R$^3$, —NHSO$_2$R$^3$ and —NHCO$_2$R$^3$, wherein R$^3$ is phenyl, naphthyl, or phenyl or naphthly substituted with one to three groups selected from C$_1$-C$_6$-alkyl, C$_6$-C$_{10}$ aryl, C$_1$-C$_6$-alkoxy and halogen.

The heteroaryl radicals include a 5- or 6-membered aromatic ring containing one to three heteroatoms selected from oxygen, sulfur and nitrogen. Examples of such heteroaryl groups are thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heteroaryl radicals may be substituted, for example, with up to three groups such as C$_1$-C$_6$-alkyl, C$_1$-C$_6$-alkoxy, substituted C$_1$-C$_6$-alkyl, halogen, C$_1$-C$_6$-alkylthio, aryl, arylthio, aryloxy, C$_2$-C$_6$-alkoxycarbonyl and C$_2$-C$_6$-alkanoylamino. The heteroaryl radicals also may be substituted with a fused ring system, e.g., a benzo or naphtho residue, which may be unsubstituted or substituted, for example, with up to three of the groups set forth in the preceding sentence. The term "halogen" is used to include fluorine, chlorine, bromine, and iodine.

The compounds of the invention which presently are preferred are formula 1 wherein R—CO is linoleoyl, stearoyl, linolenoyl, conjugated linoleoyl, palmoyl, oleoyl, arachidonyl, myristyl, lauryl, palmitoleoyl, lipoyl, 4-phenylbutyryl, cyclohexylacetyl, phenylacetyl, N-Boc 3-indolebutyryl, and pimeloyl or mixtures thereof.

An embodiment of the process according to the present invention comprises the reaction of short-chain retinyl ester 2:

2

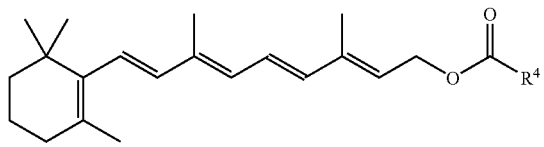

with a long-chain acid or long-chain ester in the presence of an organic solvent and an enzyme and optionally in the presence of at least one molecular sieve and/or at least one ion exchange resin to form the desired retinyl ester 1.

The substituent R$^4$ of the short-chain retinyl ester is chosen from among hydrogen, C$_1$-C$_4$ substituted or unsubstituted alkyl groups and C$_2$-C$_4$ alkenyl groups. Examples of the C$_1$-C$_4$ alkyl groups include methyl, ethyl, n-propyl, i-propyl, n-butyl, i-butyl, s-butyl and the like. Examples of the C$_2$-C$_4$ alkenyl groups include vinyl, 1-propenyl, 1-isopropenyl, 1-butenyl and the like. Preferred substituents R$^4$ include methyl and ethyl, with methyl the most preferred. The short-chain retinyl ester may be utilized in neat form or in the presence of a diluent such as a vegetable oil, wherein the percent diluent may be between 0 and 90%.

The process is carried out in an inert solvent chosen from cyclic or acyclic ether solvents such as diethyl ether, diisopropyl ether, tert-butyl methyl ether, or tetrahydrofuran, aromatic hydrocarbons such as benzene, toluene, or xylene, aliphatic or alicyclic saturated or unsaturated hydrocarbons such as hexane, heptane, cyclohexane, or limonene, halogenated hydrocarbons such as dichloromethane, dichloroethane, dibromoethane, tetrachloroethylene, or chlorobenzene, polar aprotic solvents such as acetonitrile, dimethyl formamide, or dimethyl sulfoxide, or mixtures thereof. The preferred solvents are toluene, limonene, and acetonitrile. The process may be carried out at a temperature between about −100° C. and the boiling point of the solvent, preferably about 0-60° C., most preferably 20-50° C. The amount of long-chain acid or long-chain ester may be between 0.85 and 20 equivalents based on 2, and is preferably between 1 and 10 equivalents. The enzyme used in the process is chosen from a protease, a lipase, a phospholipase, or an esterase. Preferred enzymes are lipases. These lipases may be in the form of whole cells, isolated native enzymes, or immobilized on supports. Examples of these lipases include but are not limited to Lipase PS (from *Pseudomonas* sp), Lipase PS-C (from *Psuedomonas* sp immobilized on ceramic), Lipase PS-D (from *Pseudomonas* sp immobilized on diatomaceous earth), Lipoprime 50T, Lipozyme TL IM, or Novozyme 435 (from *Candida antarctica* immobilized on acrylic resin).

The process may optionally be carried out in the presence of various addenda chosen from molecular sieves or ion exchange resins. Particularly preferred are weakly basic ion exchange resins, as the presence of these materials unexpectedly increased the conversion of 2 to 1 as compared to the same reactions without the ion exchange resins. Examples of these resins are Amberlite$^R$ or Amberlyst$^R$ weakly basic resins, such as Amberlite IRA-95, Amberlite IRA-94, and Amberlyst A-21, although it appears that any weakly basic resin will be acceptable.

The product of the process may be isolated using processes known to those of skill in the art, e.g., extraction, filtration, or crystallization. The product 1 may be purified if necessary using processes known to those of skill in the art, e.g., extraction, chromatography, distillation, or crystallization.

EXAMPLES

The novel processes provided by the present invention are further illustrated by the following examples.

Example 1

Preparation of Retinyl Linoleate with 1 Equiv of Linoleic Acid

Retinyl acetate (33 mg; 0.10 mmol) was dissolved in 5 mL of toluene. Linoleic acid (28 mg; 1.0 equiv) was added followed by 120 mg of Novozyme 435. The reaction mixture was stirred and heated at 50° C. for 1 h, at which point a sample was removed and analyzed by HPLC, indicating 49.8% conversion to retinyl linoleate with 39.8% retinyl acetate and 10.4% retinol.

HPLC (4.6×150 mm Zorbax SB-C8 column [Agilent], 3.5μ thickness, methanol eluent, detection at 350 nm): $t_R$ 4.77 min (retinyl linoleate); $t_R$ 2.32 min (retinyl acetate); $t_R$ 2.08 min (retinol).

Example 2

Preparation of Retinyl Linoleate with 1 Equiv of Linoleic Acid in the Presence of Organophilic Molecular Sieves

Retinyl acetate (33 mg; 0.10 mmol) was dissolved in 5 mL of toluene and added to 100 mg of organophilic molecular sieves. Linoleic acid (28 mg; 1.0 equiv) was added followed by 120 mg of Novozyme 435. The reaction mixture was stirred and heated at 50° C. for 1 h, at which point a sample was removed and analyzed by HPLC, indicating 53.2% conversion to retinyl linoleate with 14.4% retinyl acetate and 32.4% retinol.

Example 3

Preparation of Retinyl Linoleate with 1 Equiv of Linoleic Acid in the Presence of Amberlite IRA-95

Retinyl acetate (33 mg; 0.10 mmol) was dissolved in 5 mL of toluene and added to 50 mg of dried Amberlite IRA-95. Linoleic acid (28 mg; 1.0 equiv) was added followed by 120 mg of Novozyme 435. The reaction mixture was stirred at RT for 2 h, at which point a sample was removed and analyzed by HPLC, indicating 72.3% conversion to retinyl linoleate with 16.3% retinyl acetate and 11.3% retinol. Stirring for an additional 2 days afforded no further change.

Example 4

Preparation of Retinyl Linoleate with 1 Equiv of Linoleic Acid in the Presence of Amberlyst A-21

Retinyl acetate (33 mg; 0.10 mmol) was dissolved in 5 mL of toluene and added to 50 mg of dried Amberlyst A-21. Linoleic acid (28 mg; 1.0 equiv) was added followed by 120 mg of Novozyme 435. The reaction mixture was stirred at RT for 2 h, at which point a sample was removed and analyzed by HPLC, indicating 71.7% conversion to retinyl linoleate with 17.7% retinyl acetate and 10.6% retinol. Stirring for an additional 2 days afforded no further change.

Example 5

Preparation of Retinyl Linoleate with 2 Equiv of Linoleic Acid

Retinyl acetate (33 mg; 0.10 mmol) was dissolved in 5 mL of toluene. Linoleic acid (56 mg; 2.0 equiv) was added followed by 120 mg of Novozyme 435. The reaction mixture was stirred at ambient temperature for 2 h, at which point a sample was removed and analyzed by HPLC, indicating 63.4% conversion to retinyl linoleate with 30.5% retinyl acetate and 4.8% retinol.

Example 6

Preparation of Retinyl Linoleate with 2 Equiv of Linoleic Acid in the Presence of Amberlyst A-21

Retinyl acetate (33 mg; 0.10 mmol) was dissolved in 5 mL of toluene and added to 50 mg of dried Amberlyst A-21. Linoleic acid (56 mg; 2.0 equiv) was added followed by 120 mg of Novozyme 435. The reaction mixture was stirred at RT for 2 h, at which point a sample was removed and analyzed by HPLC, indicating 79.0% conversion to retinyl linoleate with 14.1% retinyl acetate and 6.9% retinol. Stirring overnight afforded no further change.

Example 7

Preparation of Retinyl Linoleate in Vegetable Oil with 2 Equiv of Linoleic Acid

Retinyl acetate (52% in vegetable oil, 63 mg; 0.10 mmol) was dissolved in 5 mL of toluene. Linoleic acid (56 mg; 2.0 equiv) was added followed by 120 mg of Novozyme 435. The reaction mixture was stirred and heated at 50° C. for 1 h, at which point a sample was removed and analyzed by HPLC, indicating 71.7% conversion to retinyl linoleate with 18.0% retinyl acetate and 10.2% retinol.

Example 8

Preparation of Retinyl Linoleate with 5 Equiv of Linoleic Acid

Retinyl acetate (33 mg; 0.10 mmol) was dissolved in 5 mL of toluene. Linoleic acid (140 mg; 2.0 equiv) was added followed by 120 mg of Novozyme 435. The reaction mixture was stirred at ambient temperature for 2 h, at which point a sample was removed and analyzed by HPLC, indicating 78.7% conversion to retinyl linoleate with 17.6% retinyl acetate and 3.7% retinol.

Example 9

Preparation of Retinyl Linoleate with 5 Equiv of Linoleic Acid in the Presence of Amberlyst A-21

Retinyl acetate (33 mg; 0.10 mmol) was dissolved in 5 mL of toluene and added to 50 mg of dried Amberlyst A-21. Linoleic acid (140 mg; 5.0 equiv) was added followed by 120 mg of Novozyme 435. The reaction mixture was stirred at RT for 2 h, at which point a sample was removed and analyzed by HPLC, indicating 87.4% conversion to retinyl linoleate with 9.2% retinyl acetate and 3.4% retinol. Stirring overnight afforded no further change.

Example 10

Preparation of Retinyl Linoleate in Vegetable Oil with 5 Equiv of Linoleic Acid

Retinyl acetate (52% in vegetable oil, 63 mg; 0.10 mmol) was dissolved in 5 mL of toluene. Linoleic acid (140 mg; 5.0 equiv) was added followed by 120 mg of Novozyme 435. The reaction mixture was stirred and heated at 50° C. for 1 h, at which point a sample was removed and analyzed by HPLC, indicating 83.0% conversion to retinyl linoleate with 10.9% retinyl acetate and 6.2% retinol.

Example 11

Preparation of Retinyl Linoleate with 2 Equiv of Linoleic Acid in Acetonitrile

Retinyl acetate (500 mg; 1.52 mmol) was dissolved in 3.5 mL of acetonitrile with sonication. Linoleic acid (850 mg; 3.04 mmol; 2.0 equiv) was added followed by 120 mg of Novozyme 435. The reaction mixture was stirred at RT for 19 h, at which point a sample was removed and analyzed by HPLC, indicating 28.7% conversion to retinyl linoleate with 70.8% retinyl acetate and 0.5% retinol.

Example 12

Preparation of Retinyl Linoleate with 2 Equiv of Linoleic Acid in Acetonitrile with Amberlyst A-21

Retinyl acetate (500 mg; 1.52 mmol) was dissolved in 3.5 mL of acetonitrile with sonication. Dried Amberlyst A-21 (0.25 g) was added. Linoleic acid (850 mg; 3.04 mmol; 2.0 equiv) was added followed by 120 mg of Novozyme 435. The reaction mixture was stirred at RT for 19 h, at which point a sample was removed and analyzed by HPLC, indicating 58.5% conversion to retinyl linoleate with 40.0% retinyl acetate and 1.6% retinol.

Example 13

Preparation of Retinyl Linoleate with 2 Equiv of Linoleic Acid in Limonene

Retinyl acetate (500 mg; 1.52 mmol) and linoleic acid (850 mg; 3.04 mmol; 2.0 equiv) were dissolved in 3.5 mL of limonene. Novozyme 435 (120 mg) was added and the reaction mixture was stirred at RT for 23 h, at which point a sample was removed and analyzed by HPLC, indicating 65.8% conversion to retinyl linoleate with 32.3% retinyl acetate and 1.9% retinol.

Example 14

Preparation of Retinyl Linoleate with 2 Equiv of Linoleic Acid in Limonene with Amberlyst A-21

Retinyl acetate (500 mg; 1.52 mmol) and linoleic acid (850 mg; 3.04 mmol; 2.0 equiv) were dissolved in 3.5 mL of limonene. Dried Amberlyst A-21 (0.25 g) and Novozyme 435 (120 mg) were added and the reaction mixture was stirred at RT for 23 h, at which point a sample was removed and analyzed by HPLC, indicating 90.3% conversion to retinyl linoleate with 8.5% retinyl acetate and 1.2% retinol.

Example 15

Preparation of Retinyl Linoleate with 2 Equiv of Linoleic Acid and Product Isolation Retinyl acetate (4.11 g; 12.5 mmol) and linoleic acid (7.01 g; 25.0 mmol; 2.0 equiv) were dissolved in 35 mL of toluene. Novozyme 435 (1.0 g) and dried Amberlyst A-21 (2.1 g) were added, and the reaction mixture was evacuated and filled with nitrogen ten times. The reaction mixture was stirred in the dark at ambient temperature for 5.5 h, at which point HPLC analysis indicated 90.3% conversion to retinyl linoleate (9.1% retinyl acetate and 0.6% retinol). The reaction mixture was filtered and concentrated, then concentrated twice with heptane (10 mL each). The residue was dissolved in heptane (50 mL) and washed with 2×80 mL with a 1:1 mixture of 10% aqueous potassium carbonate and methanol. The organic layer was washed further with a mixture of saturated sodium bicarbonate (10 mL), water (30 mL), and methanol (40 mL), dried (sodium sulfate) and concentrated to afford 5.14 g (75%) of a yellow oil. A portion of this material (4.00 g) was dissolved in 40 mL of heptane and washed with 20 mL of methanol. The heptane layer was concentrated to afford 3.77 g (71% overall) of retinyl linoleate. Analysis of this product indicated 90.9% retinyl linoleate (HPLC area percent), 0.26 wt % linoleic acid, and 0.06 wt % retinol. The initial aqueous extracts (using a 1:1 mixture of 10% aqueous potassium carbonate and methanol) were acidified to pH 1 with 25 mL of 3 M HCl. The resulting mixture was extracted with 20 mL of heptane. The organic solution was dried with sodium sulfate and concentrated to afford 3.91 g (56% of initial charge) of recovered linoleic acid, which is suitable for re-use.

Example 16

Preparation of Retinyl Linoleate with 1 Equiv of Methyl Linoleate

Retinyl acetate (33 mg; 0.10 mmol) was dissolved in 5 mL of toluene. Methyl linoleate (30 mg; 1.0 equiv) was added followed by 120 mg of Novozyme 435. The reaction mixture was stirred overnight at RT, at which point a sample was removed and analyzed by HPLC, indicating 49.3% conversion to retinyl linoleate with 36.9% retinyl acetate and 13.8% retinol.

Example 17

Preparation of Retinyl Linoleate with 1 Equiv of Linoleic Acid Using Lipase PS

Retinyl acetate (33 mg; 0.10 mmol) was dissolved in 5 mL of toluene. Linoleic acid (28 mg; 1.0 equiv) was added followed by 120 mg of Lipase PS (Amano). The reaction mixture was stirred at ambient temperature for 45 h, at which point a sample was removed and analyzed by HPLC, indicating 1.4% conversion to retinyl linoleate with 97.5% retinyl acetate and 1.1% retinol.

Example 18

Preparation of Retinyl Linoleate with 1Equiv of Linoleic Acid Using Lipase PS in the Presence of Amberlyst A-21

Retinyl acetate (33 mg; 0.10 mmol) was dissolved in 5 mL of toluene and added to 50 mg of dried Amberlyst A-21. Linoleic acid (28 mg; 1.0 equiv) was added followed by 120 mg of Lipase PS (Amano). The reaction mixture was stirred at ambient temperature for 45 h, at which point a sample was removed and analyzed by HPLC, indicating 10.0% conversion to retinyl linoleate with 87.3% retinyl acetate and 2.7% retinol.

Example 19

Preparation of Retinyl Linoleate with 1 Equiv of Linoleic acid Using Lipase PS-C Retinyl acetate (33 mg; 0.10 mmol) was dissolved in 5 mL of toluene. Linoleic acid (28 mg; 1.0 equiv) was added followed by 120 mg of Lipase PS-C (Amano). The reaction mixture was stirred at ambient temperature for 45 h, at which point a sample was removed and analyzed by HPLC, indicating 46.1% conversion to retinyl linoleate with 48.7% retinyl acetate and 5.2% retinol.

Example 20

Preparation of Retinyl Linoleate with 1 Equiv of Linoleic Acid Using Lipase PS-C in the Presence of Amberlyst A-21

Retinyl acetate (33 mg; 0.10 mmol) was dissolved in 5 mL of toluene and added to 50 mg of dried Amberlyst A-21. Linoleic acid (28 mg; 1.0 equiv) was added followed by 120 mg of Lipase PS-C (Amano). The reaction mixture was stirred at ambient temperature for 45 h, at which point a sample was removed and analyzed by HPLC, indicating 68.8% conversion to retinyl linoleate with 23.6% retinyl acetate and 7.6% retinol.

Example 21

Preparation of Retinyl Linoleate with 1 Equiv of Linoleic Acid Using Lipase PS-D Retinyl acetate (33 mg; 0.10 mmol) was dissolved in 5 mL of toluene. Linoleic acid (28 mg; 1.0 equiv) was added followed by 120 mg of Lipase PS-D (Amano). The reaction mixture was stirred at ambient temperature for 45 h, at which point a sample was removed and analyzed by HPLC, indicating 35.4% conversion to retinyl linoleate with 63.4% retinyl acetate and 1.2% retinol.

Example 22

Preparation of Retinyl Linoleate with 1 Equiv of Linoleic Acid Using Lipase PS in the Presence of Amberlyst A-21

Retinyl acetate (33 mg; 0.10 mmol) was dissolved in 5 mL of toluene and added to 50 mg of dried Amberlyst A-21. Linoleic acid (28 mg; 1.0 equiv) was added followed by 120 mg of Lipase PS-D (Amano). The reaction mixture was stirred at ambient temperature for 45 h, at which point a sample was removed and analyzed by HPLC, indicating 69.2% conversion to retinyl linoleate with 25.8% retinyl acetate and 5.0% retinol.

Example 23

Preparation of Retinyl Linoleate with 1 Equiv of Linoleic Acid Using Lipozyme TI IM Retinyl acetate (33 mg; 0.10 mmol) was dissolved in 5 mL of toluene. Linoleic acid (28 mg; 1.0 equiv) was added followed by 120 mg of Lipozyme TI IM (Novozyme). The reaction mixture was stirred at ambient temperature for 45 h, at which point a sample was removed and analyzed by HPLC, indicating 2.0% conversion to retinyl linoleate with 94.9% retinyl acetate and 3.2% retinol.

Example 24

Preparation of Retinyl Linoleate with 1 Equiv of Linoleic Acid Using Lipozyme TI IM in the Presence of Amberlyst A-21

Retinyl acetate (33 mg; 0.10 mmol) was dissolved in 5 mL of toluene and added to 50 mg of dried Amberlyst A-21. Linoleic acid (28 mg; 1.0 equiv) was added followed by 120 mg of Lipozyme TI IM (Novozyme). The reaction mixture was stirred at ambient temperature for 45 h, at which point a sample was removed and analyzed by HPLC, indicating 14.6% conversion to retinyl linoleate with 84.7% retinyl acetate and 0.7% retinol.

Example 25

Semi-batch Preparation of Retinyl Linoleate

Retinyl acetate (22.0 g; 80% in oil; 53.6 mmol) and linoleic acid (Pamolyn 200; 15.0 g; 53.6 mmol; 1.0 equiv) were dissolved in 160 mL of toluene in a 500 mL flask. A dip tube in the flask was connected through a peristaltic pump to a column containing 6.0 g of Novozyme 435 which was connected in sequence to a second column containing 6.0 g of dried Amberlyst A-21. A tube from this second column returned to the original flask. The pump was started (flow rate 6 mL/min) sending the reaction mixture through the two columns and then back to the pot. After 6 h conversion had reached 71%, and the pump was stopped and the Amberlyst resin was regenerated by removing the column and washing the contents with 100 mL of 10% triethylamine in toluene (with 100 mL of toluene chaser). The apparatus was reassembled and the pump re-started. After 3 more hours conversion had reached 75% and the pump was stopped. Approximately 50% of the contents of the pot (80 mL) was removed and a mixture of 11.0 g of 80% retinyl acetate and 7.5 g of linoleic acid in 80 mL of toluene was added to the pot to serve as a first reactant replenishment. The Amberlyst resin was regenerated as above, the apparatus reassembled, and the pump started. After 9 h 73.6% conversion had been achieved and the pump was stopped. Approximately 50% of the contents of the pot (80 mL) was removed and a mixture of 11.0 g of 80% retinyl acetate and 7.5 g of linoleic acid in 80 mL of toluene was added to the pot to serve as a second replenishment. The Amberlyst resin was regenerated as above, the apparatus reassembled, and the pump started. After 12 h 75.0% conversion had been achieved and the reaction was stopped.

Example 26

Preparation of the Conjugated Linoleic Acid Ester of Retinol (Retinyl-CLA) with Pamolyn 380 Conjugated Linoleic Acid in the Presence of Amberlyst A-21

Retinyl acetate (1.00 g; 3.04 mmol) was dissolved in 8.5 mL of toluene and Pamolyn 380 conjugated linoleic acid (1.71 g; 6.09 mmol; 2.0 equiv) was added followed by 120 mg of Novozyme 435 and 0.5g of dried Amberlyst A-21. The reaction mixture was stirred at RT for 15 h, at which point a sample was removed and analyzed by HPLC, indicating 87.2% conversion to retinyl-CLA with 10.9% retinyl acetate and 2.0% retinol. The reaction mixture was filtered and concentrated, then concentrated twice with heptane (10 mL each). The residue was dissolved in heptane (15 mL) and washed with 2×20 mL with a 1:1 mixture of 10% aqueous potassium carbonate and methanol. The organic layer was washed further with a mixture of saturated sodium bicarbonate (2.5 mL), water (7.5 mL), and methanol (10 mL), dried (sodium sulfate) and concentrated to afford 1.34 g (80%) of a yellow oil. Analysis of this product indicated 90.5% retinyl-CLA (HPLC area percent), 0.4 wt % conjugated linoleic acid, and 0.13% retinol. HPLC (4.6×150 mm Zorbax SB-C8 column [Agilent], 3.5µ thickness, methanol eluent, detection at 350 nm): $t_R$ 4.39, 4.88, 5.65, 6.06 min (retinyl-CLA isomers); $t_R$ 2.32 min (retinyl acetate); $t_R$ 2.08 min (retinol).

Example 27

Preparation of the Conjugated Linoleic Acid Ester of Retinol (Retinyl-CLA) with Tonalin FFA Conjugated Linoleic Acid in the Presence of Amberlyst A-21

Retinyl acetate (1.00 g; 3.04 mmol) was dissolved in 8.5 mL of toluene and Tonalin FFA conjugated linoleic acid (1.71 g; 6.09 mmol; 2.0 equiv) was added followed by 120 mg of Novozyme 435 and 0.5g of dried Amberlyst A-21. The reaction mixture was stirred at RT for 15 h, at which point a sample was removed and analyzed by HPLC, indicating 88.6% conversion to retinyl-CLA with 9.7% retinyl acetate and 1.7% retinol. The reaction mixture was filtered and concentrated, then concentrated twice with heptane (10 mL each). The residue was dissolved in heptane (15 mL) and washed with 2×20 mL with a 1:1 mixture of 10% aqueous potassium carbonate and methanol. The organic layer was washed further with a mixture of saturated sodium bicarbonate (2.5 mL), water (7.5 mL), and methanol (10 mL), dried (sodium sulfate) and concentrated to afford 1.29 g (77%) of a yellow oil. Analysis of this product indicated 92.8% retinyl-CLA (HPLC area percent), 0.8 wt % conjugated linoleic acid, and 0.1% retinol.

Example 28

Preparation of Retinyl Palmitate in the Presence of Amberlyst A-21

Retinyl acetate (1.00 g; 3.04 mmol) was dissolved in 8.5 mL of toluene and palmitic acid (1.56 g; 6.09 mmol; 2.0 equiv) was added followed by 120 mg of Novozyme 435 and 0.5g of dried Amberlyst A-21. The reaction mixture was stirred at RT for 15 h, at which point a sample was removed and analyzed by HPLC, indicating 89.2% conversion to retinyl palmitate with 9.1% retinyl acetate and 1.7% retinol. The reaction mixture was filtered and concentrated, then concentrated twice with heptane (10 mL each). The residue was dissolved in heptane (15 mL) and washed with 2×20 mL with a 1:1 mixture of 10% aqueous potassium carbonate and methanol. The organic layer was washed further with a mixture of saturated sodium bicarbonate (2.5 mL), water (7.5 mL), and methanol (10 mL), dried (sodium sulfate) and concentrated to afford 1.25 g (78%) of a yellow oil. Analysis of this product indicated 91.2% retinyl palmitate (HPLC area percent), 0.4 wt % palmitic acid, and 0.2% retinol. HPLC (4.6×150 mm Zorbax SB-C8 column [Agilent], 3.5µ thickness, methanol eluent, detection at 350 nm): $t_R$ 5.52 min (retinyl palmitate); $t_R$ 2.32 min (retinyl acetate); $t_R$ 2.08 min (retinol).

Example 29

Preparation of Retinyl Oleate in the Presence of Amberlyst A-21

Retinyl acetate (1.00 g; 3.04 mmol) and dried Amberlyst A-21 (0.5 g) were combined with 8.5 mL of toluene. Oleic acid (1.72 g; 6.09 mmol; 2.0 equiv) was added followed by 120 mg of Novozyme 435. The reaction mixture was stirred at RT for 15 h, at which point a sample was removed and analyzed by HPLC, indicating 89.2% conversion to retinyl oleate with 9.0% retinyl acetate and 1.9% retinol. The reaction mixture was filtered and concentrated, then concentrated twice with heptane (10 mL each). The residue was dissolved in heptane (15 mL) and washed with 2×20 mL with a 1:1 mixture of 10% aqueous potassium carbonate and methanol. The organic layer was washed further with a mixture of saturated sodium bicarbonate (2.5 mL), water (7.5 mL), and methanol (10 mL), dried (sodium sulfate) and concentrated to afford 1.16 g (69%) of a yellow oil. HPLC (4.6×150 mm Zorbax SB-C8 column [Agilent], 3.5µ thickness, methanol eluent, detection at 350 nm): $T_R$ 5.65 min (retinyl oleate); $T_R$ 2.32 min (retinyl acetate); $T_R$ 2.08 min (retinol).

Example 30

Preparation of Retinyl Lipoate in the Presence of Amberlyst A-21

Retinyl acetate (1.00 g; 3.04 mmol) and lipoic acid (1.26 g; 6.09 mmol; 2.0 equiv) were combined with dried Amberlyst A-21 (0.5 g). Toluene (3.5 mL) was added and the mixture was sonicated and 120 mg of Novozyme 435 was added. The reaction mixture was stirred at RT for 21 h, at which point a sample was removed and analyzed by HPLC, indicating 85.3% conversion to retinyl lipoate with 12.8% retinyl acetate and 1.9% retinol. The reaction mixture was filtered and concentrated, and the residue was dissolved in 1:1 ethyl acetate: heptane (20 mL). The solution was washed with 10 mL of a 10% aqueous potassium carbonate followed by 10 mL of a mixture of saturated sodium bicarbonate (5 mL) and water (5 mL). The organic solution was dried (sodium sulfate) and concentrated to afford 1.06 g (71%) of a yellow oil.

HPLC (4.6×150 mm Zorbax SB-C8 column [Agilent], 3.5µ thickness, methanol eluent, detection at 350 nm): $T_R$ 2.68 min (retinyl lipoate); $T_R$ 2.32 min (retinyl acetate); $T_R$ 2.08 min (retinol).

Example 31

Preparation of Retinyl 4-Phenylbutyrate in the Presence of Amberlyst A-21

Retinyl acetate (250 mg; 0.76 mmol) and 4-phenylbutyric acid (125 mg; 0.76 mmol; 1.0 equiv) were combined with dried Amberlyst A-21 (125 mg). Toluene (2.5 mL) was added and 120 mg of Novozyme 435 was added. The reaction mixture was stirred at RT for 21 h, at which point a sample was removed and analyzed by HPLC, indicating 67.8% conversion to retinyl 4-phenylbutyrate with 24.3% retinyl acetate and 7.8% retinol. A corresponding reaction without Amberlyst A-21 afforded 50.4% conversion.

HPLC (4.6×150 mm Zorbax SB-C8 column [Agilent], 3.5µ thickness, methanol eluent, detection at 350 nm): $T_R$ 2.56 min (retinyl 4-phenylbutyrate); $T_R$ 2.32 min (retinyl acetate); $T_R$ 2.08 min (retinol).

Example 32

Preparation of Retinyl Cyclohexylacetate in the Presence of Amberlyst A-21

Retinyl acetate (500 mg; 1.52 mmol) and cyclohexylacetic acid (216 mg; 1.52 mmol; 1.0 equiv) were combined with dried Amberlyst A-21 (0.25 g). Toluene (3.5 mL) was added and 120 mg of Novozyme 435 was added. The reaction mixture was stirred at RT for 18 h, at which point a sample was removed and analyzed by HPLC, indicating 64.6% conversion to retinyl cyclohexylacetate with 33.5% retinyl acetate and 1.8% retinol. A corresponding reaction without Amberlyst A-21 afforded 44.2% conversion.

HPLC (4.6×150 mm Zorbax SB-C8 column [Agilent], 3.5μ thickness, elution with 80:20 methanol:water(0.1% TFA) for 15 min, gradient to 100% methanol over 10 min, hold at 100% methanol for 5 min, detection at 350 nm): $T_R$ 26.1 min (retinyl cyclohexylacetate); $T_R$ 21.1 min (retinyl acetate); $t_R$ 11.8 min (retinol).

Example 33

Preparation of Retinyl Phenylacetate in the Presence of Amberlyst A-21

Retinyl acetate (500 mg; 1.52 mmol) and phenylacetic acid (207 mg; 1.52 mmol; 1.0 equiv) were combined with dried Amberlyst A-21 (0.25 g). Toluene (3.5 mL) was added and 120 mg of Novozyme 435 was added. The reaction mixture was stirred at RT for 19 h, at which point a sample was removed and analyzed by HPLC, indicating 58.5% conversion to retinyl phenylacetate with 40.0% retinyl acetate and 1.6% retinol. A corresponding reaction without Amberlyst A-21 afforded 28.7% conversion.

HPLC (4.6×150 mm Zorbax SB-C8 column [Agilent], 3.5μ thickness, methanol eluent, detection at 350 nm): $T_R$ 4.67 min (retinyl phenylacetate); $T_R$ 2.32 min (retinyl acetate); $T_R$ 2.08 min (retinol).

Example 34

Preparation of Retinyl N-Boc 3-Indolebutyrate

Retinyl acetate (33 mg; 0.10 mmol) and N-Boc indole-3-butyric acid (31 mg; 0.10 mmol; 1.0 equiv) were combined. Toluene (3.5 mL) was added and 120 mg of Novozyme 435 was added. The reaction mixture was stirred at 50° C. for 4 days, at which point a sample was removed and analyzed by HPLC, indicating 50.6% conversion to retinyl N-Boc 3-Indolebutyrate with 44.8% retinyl acetate and 4.6% retinol.

HPLC (4.6×150 mm Zorbax SB-C8 column [Agilent], 3.5μ thickness, elution with 80:20 methanol:water (0.1%TFA) for 15 min, gradient to 100% methanol over 10 min, hold at 100% methanol for 5 min, detection at 350 nm): $T_R$ 26.7 min (retinyl N-Boc 3-Indolebutyrate); $T_R$ 21.1 min (retinyl acetate); $T_R$ 11.8 min (retinol).

Example 35

Preparation of Retinyl Pimelate

Retinyl acetate (500 mg; 1.52 mmol) and pimelic acid (488 mg; 3.04 mmol; 2.0 equiv) were combined. Toluene (5.0 mL) was added and 120 mg of Novozyme 435 was added. The reaction mixture was stirred at RT for 2 days, at which point a sample was removed and analyzed by HPLC, indicating 36.5% conversion to a mixture of retinyl pimelate and di-retinyl pimelate with 61.8% retinyl acetate and 1.8% retinol.

HPLC (4.6×150 mm Zorbax SB-C8 column [Agilent], 3.5μ thickness, elution with 80:20 methanol:water (0.1%TFA) for 15 min, gradient to 100% methanol over 10 min, hold at 100% methanol for 5 min, detection at 350 nm): $T_R$ 20.3, 29.0 min (retinyl pimelate and diretinyl pimelate); $T_R$ 21.1 min (retinyl acetate); $T_R$ 11.8 min (retinol).

The invention has been described in detail with particular reference to preferred embodiments thereof, but it will be understood that variations and modifications can be effected within the spirit and scope of the invention.

We claim:
1. A process for preparing a long-chain retinyl ester, comprising:
reacting a short-chain retinyl ester according to formula 2:

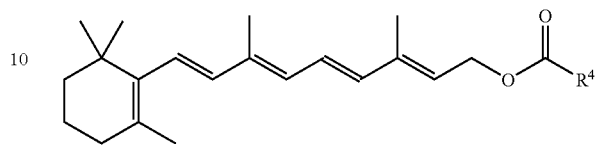

with a long-chain acid or long-chain ester in the presence of an organic solvent and a lipase to form the long-chain retinyl ester,
wherein $R^4$ is selected from the group consisting of hydrogen, $C_1$-$C_4$ alkyl groups and $C_2$-$C_4$ alkenyl groups;
the lipase is in a whole cell, an isolated native enzyme, or immobilized on a support, and
the process is carried out in the presence of an ion exchange resin.

2. The process according to claim 1, wherein the $C_1$-$C_4$ alkyl groups include at least one of methyl, ethyl, n-propyl, i-propyl, n-butyl, i-butyl, and s-butyl.

3. The process according to claim 1, wherein the $C_2$-$C_4$ alkenyl groups include at least one of vinyl, 1-propenyl, 1-isopropenyl, and 1-butenyl.

4. The process according to claim 1 wherein $R^4$ is a methyl or an ethyl.

5. The process according to claim 1, wherein $R^4$ is a methyl.

6. The process according to claim 1, wherein the short-chain retinyl ester is in neat form or in a diluent.

7. The process according to claim 6, wherein the diluent is a vegetable oil and is present in an amount of between 0 and 90%.

8. The process according to claim 1, wherein the process is carried out in an inert solvent selected from the group consisting of an ether solvent, a hydrocarbon solvent, a polar aprotic solvent, and mixtures thereof.

9. The process according to claim 8, wherein the ether solvent is selected from the group consisting of diethyl ether, diisopropyl ether, tert-butyl methyl ether, tetrahydrofuran and mixtures thereof.

10. The process according to claim 8, wherein the hydrocarbon solvent is selected from the group consisting of benzene, toluene, xylene, hexane, heptane, cyclohexane, limonene, dichloromethane, dichloroethane, dibromoethane, tetrachloroethylene, chlorobenzene, and mixtures thereof.

11. The process according to claim 8, wherein the polar aprotic solvent is selected from the group consisting of acetonitrile, dimethyl formamide, dimethyl sulfoxide, and mixtures thereof.

12. The process according to claim 1, wherein the process is carried out at a temperature between about –100° C. and the boiling point of the solvent.

13. The process according to claim 12, wherein the temperature is between about 0-60° C.

14. The process according to claim 13, wherein the temperature is between about 20-50° C.

15. The process according to claim 1, wherein the long-chain acid or long-chain ester is present in an amount between about 0.85 and 20 equivalents based on an amount of the short-chain retinyl ester.

16. The process according to claim 15, wherein the long-chain acid or long-chain ester is present in an amount between about 1.0 and 10 equivalents based on an amount of the short-chain retinyl ester.

17. The process according to claim 1, wherein the ion exchange resin is a basic ion exchange resin.

18. The process according to claim 17, wherein the basic ion exchange resin is present in an amount between 10 and 1000 weight percent based on an amount of the short-chain retinyl ester.

19. The process according to claim 1, further comprising isolating the retinyl ester via extraction, chromatography, distillation, or crystallization.

20. A process for the preparation of a long-chain retinyl ester represented by the general formula 1:

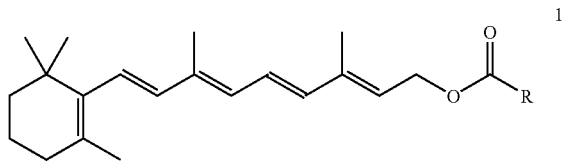

comprising:
reacting a short-chain retinyl ester with a long-chain acid or long-chain ester in the presence of an organic solvent and a lipase to form the long-chain retinyl ester,
wherein R is at least one selected from the group consisting of $C_4$-$C_{24}$ alkyl, $C_4$-$C_{24}$ alkenyl, $C_4$-$C_{24}$ dienyl, $C_6$-$C_{24}$ trienyl, $C_8$-$C_{24}$ tetraenyl, $C_3$-$C_8$ cycloalkyl, $C_6$-$C_{20}$ carbolyic aryl, and $C_4$-$C_{20}$ heteroaryl wherein the heteroaryl includes at least one of sulfur, nitrogen and oxygen
the lipase is in a whole cell, an isolated native enzyme, or immobilized on a support, and
the process is carried out in the presence of an ion exchange resin.

21. The process according to claim 20, wherein said alkyl, alkenyl, dienyl, trienyl, tetraenyl, or cycloalkyl is substituted with one to three groups selected from the group consisting of $C_1$-$C_6$-alkoxy, cyano, $C_2$-$C_6$-alkoxycarbonyl, $C_2$-$C_6$-alkanoyloxy, hydroxy, heteroaryl, thiol, thioether, disulfide, and halogen.

22. The process according to claim 20, wherein said carbocyclic aryl includes at least one of phenyl, naphthyl, and anthracenyl.

23. The process according to claim 22, wherein the phenyl, naphthyl, or anthracenyl is substituted with one to three substituents selected from the group consisting of $C_1$-$C_6$-alkyl, substituted $C_1$-$C_6$-alkyl, $C_6$-$C_{10}$ aryl, substituted $C_6$-$C_{10}$ aryl, $C_1$-$C_6$-alkoxy, halogen, carboxy, cyano, $C_1$-$C_6$-alkanoyloxy, $C_1$-$C_6$-alkylthio, $C_1$-$C_6$-alkylsulfonyl, trifluoromethyl, hydroxy, $C_2$-$C_6$-alkoxycarbonyl, $C_2$-$C_6$-alkanoylamino and —O—$R^3$, S-$R^3$, —$SO_2$-$R^3$, —$NHSO_2R^3$ and —$NHCO_2R^3$, wherein $R^3$ is phenyl, naphthyl, or phenyl or naphthly substituted with one to three groups selected from $C_1$-$C_6$-alkyl, $C_6$-$C_{10}$ aryl, $C_1$-$C_6$-alkoxy and halogen.

24. The process according to claim 20, wherein said heteroaryl includes at least one of a 5- or 6-membered aromatic ring containing one to three heteroatoms selected from oxygen, sulfur and nitrogen.

25. The process according to claim 24, wherein the heteroaryl includes at least one of thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, and indolyl.

26. The process according to claim 20, wherein the process is carried out in an inert solvent selected from the group consisting of an ether solvent, a hydrocarbon solvent, a polar aprotic solvent, and mixtures thereof.

27. The process according to claim 26, wherein the ether solvent is selected from the group consisting of diethyl ether, diisopropyl ether, tert-butyl methyl ether, tetrahydrofuran and mixtures thereof.

28. The process according to claim 26, wherein the hydrocarbon solvent is selected from the group consisting of benzene, toluene, xylene, hexane, heptane, cyclohexane, limonene, dichloromethane, dichloroethane, dibromoethane, tetrachioroethylene, chlorobenzene, and mixtures thereof.

29. The process according to claim 26, wherein the polar aprotic solvent is selected from the group consisting of acetonitrile, dimethyl formamide, dimethyl sulfoxide, and mixtures thereof.

30. The process according to claim 20, wherein the process is carried out at a temperature between about −100° C. and the boiling point of the solvent.

31. The process according to claim 30, wherein the temperature is between about 0-60° C.

32. The process according to claim 31, wherein the temperature is between about 20-50° C.

33. The process according to claim 20, wherein the long-chain acid or long-chain ester is present in an amount between about 0.85 and 20 equivalents based on an amount of the short-chain retinyl ester.

34. The process according to claim 33, wherein the long-chain acid or long-chain ester is present in an amount between about 1.0 and 10 equivalents based on an amount of the short-chain retinyl ester.

35. The process according to claim 20, wherein the ion exchange resin is a basic ion exchange resin.

36. The process according to claim 35, wherein the basic ion exchange resin is present in an amount between 10 and 1000 weight percent based on an amount of the short-chain retinyl ester.

37. The process according to claim 20, further comprising isolating the retinyl ester via extraction, chromatography, distillation, or crystallization.

* * * * *

UNITED STATES PATENT AND TRADEMARK OFFICE
CERTIFICATE OF CORRECTION

| | | |
|---|---|---|
| PATENT NO. | : 7,566,795 B2 | Page 1 of 1 |
| APPLICATION NO. | : 11/544152 | |
| DATED | : July 28, 2009 | |
| INVENTOR(S) | : Boaz et al. | |

It is certified that error appears in the above-identified patent and that said Letters Patent is hereby corrected as shown below:

Column 16, Line 26, Claim 28 "tetrachioroethylene" should read --tetrachloroethylene--.

Signed and Sealed this

Second Day of November, 2010

David J. Kappos
*Director of the United States Patent and Trademark Office*